(12) United States Patent
Walter et al.

(10) Patent No.: US 9,376,639 B2
(45) Date of Patent: Jun. 28, 2016

(54) METHOD AND SYSTEM FOR PERFORMING GASIFICATION OF CARBONACEOUS FEEDSTOCK

(71) Applicant: TerraPower, LLC, Bellevue, WA (US)

(72) Inventors: Joshua C. Walter, Kirkland, WA (US); Samuel Scott Goodrich, Philomath, OR (US)

(73) Assignee: TERRAPOWER, LLC, Bellevue, WA (US)

(*) Notice: Subject to any disclaimer, the term of this patent is extended or adjusted under 35 U.S.C. 154(b) by 0 days.

(21) Appl. No.: 14/210,288

(22) Filed: Mar. 13, 2014

(65) Prior Publication Data

US 2014/0275678 A1 Sep. 18, 2014

Related U.S. Application Data

(60) Provisional application No. 61/794,121, filed on Mar. 15, 2013.

(51) Int. Cl.
| | |
|---|---|
| *B01J 8/04* | (2006.01) |
| *C10L 1/02* | (2006.01) |
| *C10K 3/04* | (2006.01) |
| *C10J 3/46* | (2006.01) |

(52) U.S. Cl.
CPC .................. *C10L 1/023* (2013.01); *C10J 3/463* (2013.01); *C10K 3/04* (2013.01); *B01J 2208/0053* (2013.01); *B01J 2208/00106* (2013.01); *B01J 2219/00006* (2013.01); *C10G 2300/1003* (2013.01); *C10G 2300/1011* (2013.01); *C10J 2300/1246* (2013.01); *C10J 2300/1621* (2013.01); *C10J 2300/1659* (2013.01); *C10J 2300/1665* (2013.01); *C10J 2300/1853* (2013.01); *C10J 2300/1884* (2013.01); *C10J 2300/1892* (2013.01); *Y02P 30/20* (2015.11)

(58) Field of Classification Search
None
See application file for complete search history.

(56) References Cited

U.S. PATENT DOCUMENTS

| | | | |
|---|---|---|---|
| 3,890,908 A * | 6/1975 | von Klenck et al. | 110/243 |
| 5,344,848 A | 9/1994 | Steinberg et al. | |
| 2002/0031690 A1 * | 3/2002 | Shimazu et al. | 429/19 |
| 2002/0048545 A1 | 4/2002 | Lewis | |
| 2007/0286797 A1 | 12/2007 | Behrens et al. | |
| 2008/0040975 A1 * | 2/2008 | Calderon | 48/197 R |
| 2009/0077888 A1 | 3/2009 | Zander et al. | |
| 2009/0206007 A1 | 8/2009 | Allam | |
| 2010/0043445 A1 | 2/2010 | Coronella et al. | |
| 2010/0319255 A1 | 12/2010 | Struble et al. | |
| 2011/0000825 A1 | 1/2011 | McGrady et al. | |
| 2011/0180262 A1 | 7/2011 | O'Dowd | |
| 2013/0025190 A1 | 1/2013 | Cheiky et al. | |

OTHER PUBLICATIONS

PCT International Search Report; International App. No. PCT/US2014/027572; Aug. 21, 2014; 3 pages.

(Continued)

*Primary Examiner* — Jennifer A Leung

(57) ABSTRACT

The gasification of a carbonaceous material includes receiving a volume of feedstock, supplying thermal energy to the volume of feedstock to convert at least a portion of the volume of feedstock to at least one pyrolysis reaction product via at least one pyrolysis reaction, super-heating the at least one pyrolysis reaction product, providing a volume of super-heated steam, mixing the volume of super-heated steam with the super-heated at least one pyrolysis reaction product and converting at least a portion of at least one reformed product to at least one synthesis gas product via at least one water-gas-shift reaction.

26 Claims, 12 Drawing Sheets

(56) References Cited

OTHER PUBLICATIONS

PCT International Search Report; International App. No. PCT/US2014/027530; Aug. 8, 2014; 4 pages.

PCT International Preliminary Report on Patentability and Written Opinion for PCT/US2014/027572; Sep. 25, 2015.
PCT International Preliminary Report on Patentability and Written Opinion for PCT/US2014/027530; Sep. 24, 2015.

* cited by examiner

METHOD AND SYSTEM FOR PERFORMING GASIFICATION OF CARBONACEOUS FEEDSTOCK

CROSS-REFERENCE TO RELATED APPLICATION

The present application is related to and claims the benefit of the earliest available effective filing date(s) from the following listed application(s) (the "Related applications") (e.g., claims earliest available priority dates for other than provisional patent applications or claims benefits under 35 USC §119(e) for provisional patent applications, for any and all parent, grandparent, great-grandparent, etc. applications of the Related application(s)).

RELATED APPLICATIONS

For purposes of the USPTO extra-statutory requirements, the present application constitutes a regular (non-provisional) patent application of U.S. Provisional patent application entitled SYSTEMS AND METHODS FOR CONVERTING BIOMASS FEEDSTOCK TO REFINED PRODUCTS, naming JOSHUA C. WALTER and MANUEL GARCIA-PEREZ as inventors, filed Mar. 15, 2013, Application Ser. No. 61/794,121.

TECHNICAL FIELD

The present disclosure generally relates to the gasification of a carbonaceous feedstock material, and in particular, the gasification of a carbonaceous feedstock material including supercritical pyrolysis processing.

SUMMARY

In an illustrative embodiment, a method includes, but is not limited to, receiving a volume of feedstock; supplying thermal energy to the volume of feedstock to convert at least a portion of the volume of feedstock to at least one pyrolysis reaction product via at least one pyrolysis reaction; super-heating the at least one pyrolysis reaction product; providing a volume of super-heated steam; mixing the volume of super-heated steam with the super-heated at least one pyrolysis reaction product; and converting at least a portion of at least one reformed product to at least one synthesis gas product via at least one water-gas-shift reaction.

In an illustrative embodiment, a method includes, but is not limited to, receiving a volume of feedstock; supplying thermal energy to the volume of feedstock to convert at least a portion of the volume of feedstock to at least one pyrolysis reaction product via at least one pyrolysis reaction; super-heating the at least one pyrolysis reaction product; providing a volume of super-heated steam; mixing the volume of super-heated steam with the super-heated at least one pyrolysis reaction product; converting at least a portion of at least one reformed product to at least one synthesis gas product via at least one water-gas-shift reaction; compressing the at least one synthesis gas product in at least one compression phase; converting at least a portion of the compressed at least one synthesis gas product to a volume of methanol; and converting at least a portion of the volume of methanol to a volume of gasoline.

In an illustrative embodiment, an apparatus includes, but is not limited to, a pyrolysis reaction chamber for containing a volume of feedstock; a first thermal energy transfer system in thermal communication with the pyrolysis reaction chamber and at least one heat source for converting at least a portion of the volume of feedstock to at least one pyrolysis reaction product; a second thermal energy transfer system in thermal communication with an outlet of the pyrolysis reaction chamber and an internal heat source for super-heating the at least one pyrolysis reaction product; a steam generator including an outlet arranged to mix the super-heated steam with the super-heated at least one pyrolysis reaction product; a steam reformer in fluidic communication with the outlet of the pyrolysis reaction chamber and the steam generator, the steam reformer configured to convert the super-heated at least one pyrolysis reaction product and the super-heated steam to at least one reformed product; and a water-gas-shift reactor in fluidic communication with an outlet of the steam reformer and configured to convert at least a portion of the at least one reformed product to at least one synthesis gas product via at least one water-gas-shift reaction.

In an illustrative embodiment, an apparatus includes, but is not limited to, a pyrolysis reaction chamber for containing a volume of feedstock; a first thermal energy transfer system in thermal communication with the pyrolysis reaction chamber and at least one heat source for converting at least a portion of the volume of feedstock to at least one pyrolysis reaction product; a second thermal energy transfer system in thermal communication with an outlet of the pyrolysis reaction chamber and an internal heat source for super-heating the at least one pyrolysis reaction product; a steam generator including an outlet arranged to mix the super-heated steam with the super-heated at least one pyrolysis reaction product; a steam reformer in fluidic communication with the outlet of the pyrolysis reaction chamber and the steam generator, the steam reformer configured to convert the super-heated at least one pyrolysis reaction product and the super-heated steam to at least one reformed product; a water-gas-shift reactor in fluidic communication with an outlet of the steam reformer and configured to convert at least a portion of the at least one reformed product to at least one synthesis gas product via at least one water-gas-shift reaction; a compression system in fluidic communication with an outlet of the water-gas-shift reactor and configured to compress the at least one synthesis gas product in at least one compression phase; a methanol reactor in fluidic communication with an outlet of the compression system and configured to convert at least a portion of the compressed at least one synthesis gas product to a volume of methanol; and a methanol-to-gasoline reactor in fluidic communication with an outlet of the methanol reactor and configured to convert at least a portion of the volume of methanol to a volume of gasoline.

In an illustrative embodiment, a system includes, but is not limited to, at least one heat source; a pyrolysis reaction chamber for containing a volume of feedstock; a first thermal energy transfer system in thermal communication with the pyrolysis reaction chamber and the at least one heat source for converting at least a portion of the volume of feedstock to at least one pyrolysis reaction product; a second thermal energy transfer system in thermal communication with an outlet of the pyrolysis reaction chamber and an internal heat source for super-heating the at least one pyrolysis reaction product; a steam generator including an outlet arranged to mix the super-heated steam with the super-heated at least one pyrolysis reaction product; a steam reformer in fluidic communication with the outlet of the pyrolysis reaction chamber and the steam generator, the steam reformer configured to convert the super-heated at least one pyrolysis reaction product and the super-heated steam to at least one reformed product; a water-gas-shift reactor in fluidic communication with an outlet of the steam reformer and configured to convert at least a portion of the at least one reformed product to at least one synthesis gas product via at least one water-gas-shift reaction; a compression system in fluidic communication with an outlet of the water-gas-shift reactor; and configured to compress the at least one synthesis gas product in at least one compression phase; a methanol reactor in fluidic communication with an outlet of the compression system and configured to convert at least a portion of the compressed at least one synthesis gas product to a volume of methanol; and a methanol-to-gasoline reactor in fluidic communication with an outlet of the methanol reactor and configured to convert at least a portion of the volume of methanol to a volume of gasoline.

In addition to the foregoing, various other method and/or system and/or apparatus aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

DETAILED DESCRIPTION

Figure 1A:
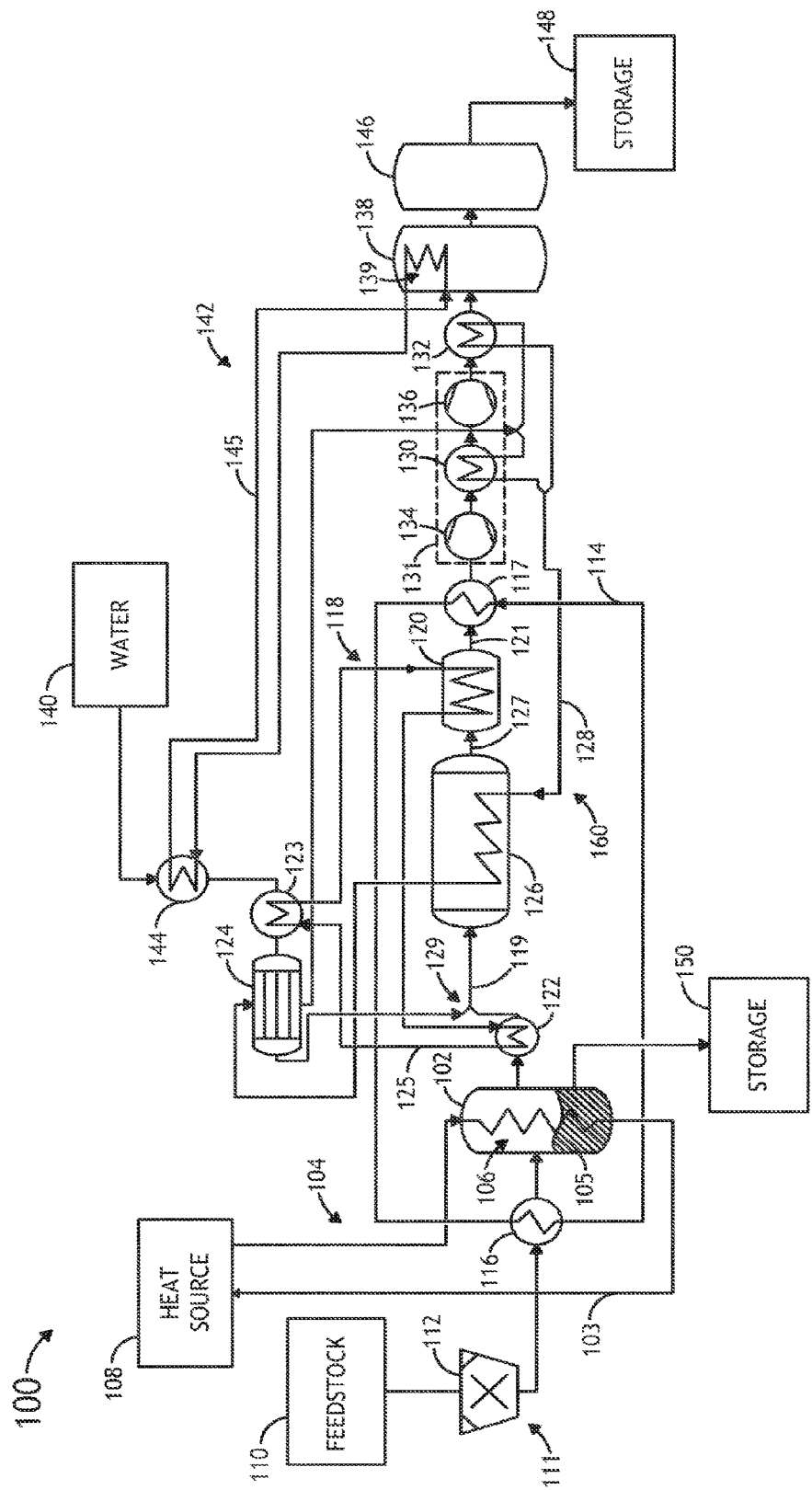
FIG. 1A is a block diagram view of a system for performing gasification of a carbonaceous feedstock material, in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Figure 1B:
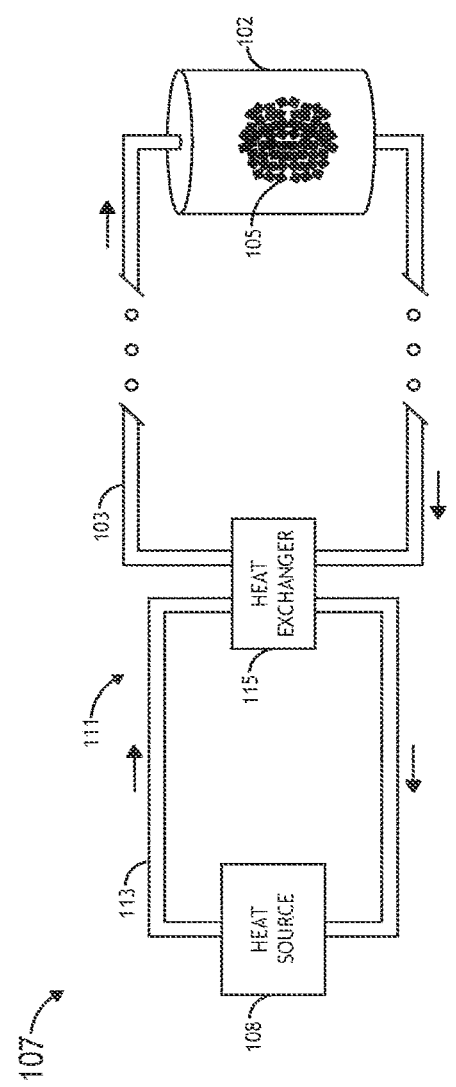
FIG. 1B is a block diagram view of an indirect heat exchange system of a system for performing gasification of a carbonaceous feedstock material, in accordance with an illustrative embodiment.
Figure 1C:
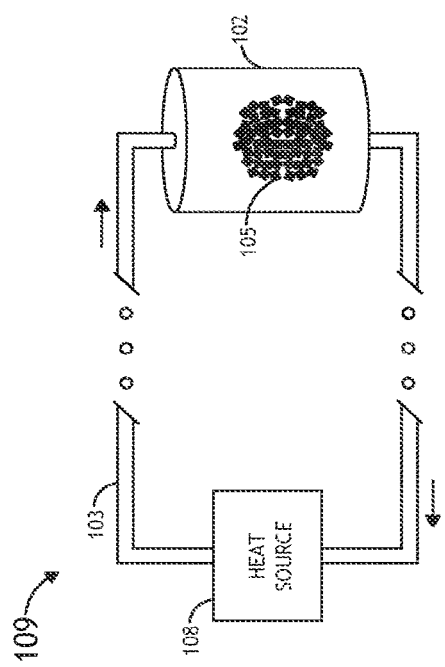
FIG. 1C is a block diagram view of a direct heat exchange system of a system for performing gasification of a carbonaceous feedstock material, in accordance with an illustrative embodiment.
Figure 1D:
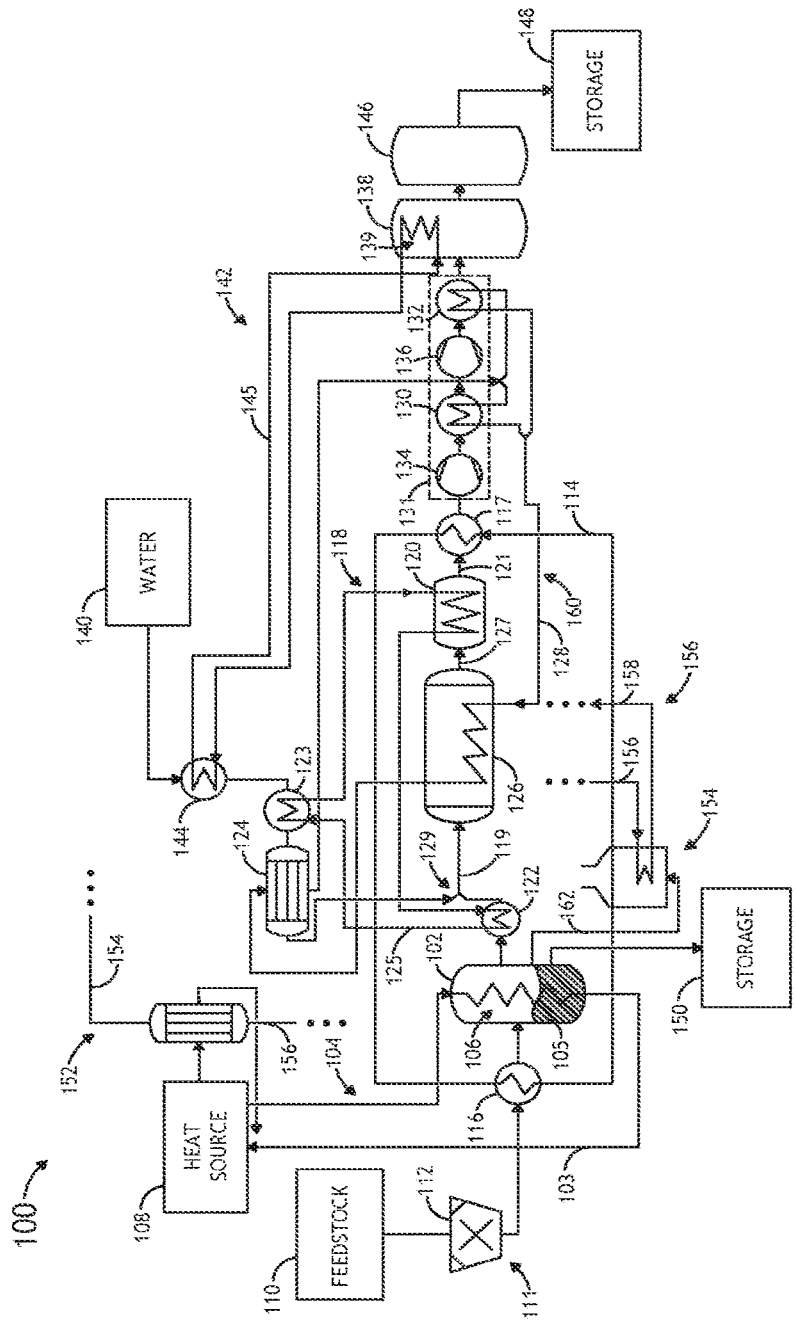
FIG. 1D is a block diagram view of a system for performing gasification of a carbonaceous feedstock material, in accordance with an illustrative embodiment.

Referring generally to FIGS. 1A and 1D, a system 100 for performing gasification of a carbonaceous feedstock is described. In one embodiment, the system 100 is suitable for converting feedstock material to a gasoline product through a series of thermochemical decomposition and treatment stages.

FIG. 1A illustrates a block diagram view of a system 100 for performing gasification of a carbonaceous feedstock, in accordance with one or more illustrative embodiments. In one embodiment, the system 100 includes a pyrolysis reaction chamber 102, such as, but not limited to, a fast pyrolysis reaction chamber or a supercritical pyrolysis chamber. In one embodiment, the pyrolysis reaction chamber 102 is suitable for containing a volume of feedstock material (e.g., carbonaceous material). In another embodiment, the system 100 includes one or more heat sources 108. In another embodiment, the system 100 includes a first thermal energy transfer system 104 in thermal communication with the pyrolysis reaction chamber 102 and the one or more heat sources 108. In another embodiment, the first thermal energy transfer system 104 is arranged to transfer thermal energy from the one or more heat sources 108 to the volume of feedstock 105 contained within the pyrolysis reaction chamber 102. In another embodiment, the first thermal energy transfer system 104 is configured to transfer thermal energy from the one or more heat sources 108 to the volume of feedstock 105 contained within the pyrolysis reaction chamber 102 in order to convert a portion of the feedstock material to one or more reaction products.

In one embodiment, the first thermal energy transfer system 104 includes a heat transfer element 103 containing a volume of a heat transfer fluid (e.g., liquid, gas, or supercritical fluid) in thermal communication (e.g., direct or indirect thermal communication) with the one or more heat sources 108. In one embodiment, the heat transfer element 103 may include, but is not limited to, a heat transfer loop, a heat transfer line and the like. For example, the heat transfer element 103 may include, but is not limited to, a heat transfer loop filled with a heat transfer fluid (e.g., pressurized heat transfer fluid) and placed in thermal communication (e.g., directly or indirectly) with one or more portions of the one or more heat sources 108. For instance, the heat transfer fluid may include, but is not limited to, a liquid (e.g., liquid metal or molten salt), a gas (e.g., pressurized gas), water or supercritical fluid (e.g., super critical carbon dioxide).

In one embodiment, the supercritical fluid based heat transfer fluid may include any supercritical fluid known in the art suitable for transferring energy from the one or more heat sources 108 to the feedstock 105 contained in the pyrolysis reaction chamber 102. In one embodiment, the supercritical fluid includes, but is not limited to, supercritical carbon dioxide. In another embodiment, the supercritical fluid includes, but is not limited to, water, methanol, ethanol, propanol, or acetone. In another embodiment, the supercritical fluid is pressurized to high pressure within at least one of the heat transfer element 103 and the pyrolysis reaction chamber 102.

It is noted herein that the supercritical fluid, such as, but not limited to, $CO_2$, may have low viscosity and surface tension, allowing such supercritical fluids to readily penetrate organic materials (e.g., biomass material). The penetration of the supercritical fluid into the feedstock 105 may reduce the need for converting the feedstock 105 into fine particles prior to a thermochemical reaction, thereby saving energy in the reaction of the feedstock material. In one embodiment, in the case where the supercritical fluid is supercritical $CO_2$, the supercritical fluid may be pressurized to above its critical pressure (72.9 atm) and critical temperature (304 K). It is noted herein that above these conditions $CO_2$ will display unique solvency properties similar to organic solvents such as hexane, methanol and ethanol. The non-polar nature of supercritical $CO_2$ may facilitate the control of undesirable ionic secondary reactions that commonly occur in aqueous environments.

In another embodiment, a supercritical fluid, such as supercritical $CO_2$, may provide strong temperature and reaction time control via the injection of cooler supercritical fluid into the pyrolysis reaction chamber 102 to quench the reaction or hotter supercritical fluid to accelerate the reaction. It is further recognized that since a number of supercritical fluids, such as supercritical CO2, can be efficiently compressed, pressure conditions within the reaction chamber 102 may also be used to control thermochemical reactions within the reaction chamber 102. The implementation of supercritical fluids to drive pyrolysis is described in U.S. patent application Ser. No. 14/209,798 to Walter et al., filed on Mar. 13, 2014, which is incorporated herein by reference in the entirety.

In one embodiment, the system 100 includes a feedstock supply system 111. In one embodiment, the feedstock supply system 111 is operably coupled to the pyrolysis reaction chamber 102. In another embodiment, the feedstock supply system 111 provides a volume of feedstock material 105 to the interior of the pyrolysis reaction chamber 102. The feedstock supply system 111 may include any supply system known in the art suitable for translating a selected amount of feedstock material, such as solid material, particulate material or liquid material, from one or more feedstock sources 110 to the interior of the pyrolysis reaction chamber 102. For example, the feedstock supply system 111 may include, but is not limited to, a conveyor system, a fluid transfer system and the like.

In another embodiment, the feedstock supply system 111 includes a pre-heater 116. In another embodiment, the system 100 includes a pre-heating heat transfer loop 114. For example, the heat transfer 114 includes a first heat exchanger 117 for transferring heat from the output of the water-gas-shift reactor (e.g., T=500°-700° C.) to the heat transfer loop 114 and a second heat exchanger 116 for transferring heat from the heat transfer loop 114 to the feedstock material.

In another embodiment, the feedstock supply system 111 includes a grinder 112. In another embodiment, the grinder 111 is suitable for grinding the feedstock from the feedstock supply 110 in order to create a feedstock material having a particle size suitable for pyrolysis reaction in the pyrolysis reaction chamber 102.

The feedstock material 105 may include any carbonaceous material known in the art. For example, the feedstock material 105 may include, but is not limited to, coal, biomass, mixed-source biomaterial, peat, tar, plastic, refuse, and landfill waste. For example, in the case of coal, the feedstock may include, but is not limited to, bituminous coal, sub-bituminous coal, lignite, anthracite and the like. By way of another example, in the case of biomass, the feedstock may include a wood material, such as, but not limited to, softwoods or hardwoods.

The one or more heat sources 108 may include any heat source known in the art suitable for providing thermal energy sufficient to heat the feedstock 105 to the selected temperature (e.g., temperature adequate for fast pyrolysis (e.g., 350-600° C.)).

In one embodiment, the one or more heat sources 108 include a non-$CO_2$ emitting heat source. In one embodiment, the one or more heat sources 108 include one or more nuclear reactors. The one or more heat sources 108 may include any nuclear reactor known in the art. For example, the one or more heat sources 108 may include a liquid metal cooled nuclear reactor, a molten salt cooled nuclear reactor, a high temperature water cooled nuclear reactor, a gas cooled nuclear reactor and the like.

It is recognized herein that a nuclear reactor may generate temperatures sufficient to carry out pyrolysis (e.g., fast pyrolysis or supercritical pyrolysis) of feedstock 105. For example, a nuclear reactor heat source may generate temperatures in excess of 350-600° C. In this regard, a nuclear reactor may be used to transfer thermal energy (e.g., at a temperature in excess of 350-600° C.) to the supercritical fluid (e.g., supercritical $CO_2$). In turn, the supercritical fluid may transfer the nuclear reactor generated thermal energy to the feedstock 105 contained within the reaction chamber 102.

It is further noted herein that a nuclear reactor heat source is particularly advantageous as a heat source because the thermochemical reaction temperatures of the reaction chamber 102 are within the range of operating temperatures for many nuclear reactors. Nuclear reactor heat may be used to create reaction products in the reaction chamber 102 at high efficiency since the nuclear reactor is operating at the reaction temperature for thermochemical conversion (i.e., heat added at the thermochemical reaction temperature supplies the required reaction enthalpy).

In one embodiment, the supercritical fluid of system 100 serves as a safety mechanism in the operation of the nuclear reactor driven system 100. By way of example, supercritical carbon dioxide may be stored in one or more reservoirs (not shown) or tanks (not shown). It is noted herein that supercritical carbon dioxide stored in this manner may be used to provide a thermal buffer between the reactor and the system 100 by acting as a thermal dashpot. In another embodiment, the supercritical fluid may be stored at temperatures and pressures suitable for discharge into thermomechanical rotating machinery, such as a turbine. In this manner, a selected amount of work may be developed by the compressed $CO_2$ to provide mechanical or electric power to safety systems, such as flow valves, safety valves, isolation valves, pumps, and the like.

In another embodiment, as shown in FIG. 1B, the first thermal energy transfer system 104 includes an indirect heat exchange system 107. In one embodiment, the indirect heat exchange system 107 is configured to indirectly transfer thermal energy from the one or more heat sources 108 to the volume of the heat transfer fluid contained within the heat transfer element 103. In one one embodiment, the indirect heat exchange system 107 includes an intermediate heat transfer element 111 configured to transfer thermal energy from the one or more heat sources 108 to the intermediate heat transfer element 111. In turn, the intermediate heat transfer element 111 may transfer thermal energy from the intermediate heat transfer element 111 to the volume of the heat transfer fluid contained within the heat transfer element 103.

In one embodiment, the intermediate heat transfer element 111 may include an intermediate heat transfer loop 113, and one or more heat exchangers 115. In one embodiment, the intermediate heat transfer loop 113 may include any working fluid known in the art suitable for transferring thermal energy. For example, the working fluid of the intermediate heat transfer loop 113 may include, but is not limited to, a liquid salt, a liquid metal, a gas, a supercritical fluid (e.g., supercritical $CO_2$) or water.

In another embodiment, the intermediate heat transfer element 111 includes a heat exchanger 115 in thermal communication with the intermediate heat transfer loop 113 and the heat transfer element 103. For example, in the case where the one or more heat sources 108 include a nuclear reactor, one or more coolant systems (e.g., primary, intermediate or ternary) of the nuclear reactor (e.g., a molten salt cooled nuclear reactor, a liquid metal cooled reactor, a gas cooled reactor or and a supercritical fluid cooled reactor) may be coupled to the intermediate heat transfer loop 113 directly or indirectly. In turn, upon transferring thermal energy from the nuclear reactor to the intermediate heat transfer loop 113, the intermediate heat transfer loop 113 may transfer the nuclear reactor generated thermal energy from the intermediate transfer loop 113 to the heat transfer fluid contained within the heat transfer element 103 via a heat exchanger 115.

In one embodiment, as shown in FIG. 1C, the first thermal energy transfer system 104 includes a direct heat exchange system 109 configured to transfer thermal energy directly from the one or more heat sources 108 to the volume of the heat transfer fluid (e.g., supercritical fluid) of the heat transfer element 103. For example, the heat transfer element 103 may be placed in direct thermal communication with a portion of the one or more heat sources 108. For instance, in the case where the one or more heat sources 108 includes a nuclear reactor, one or more coolant systems of the nuclear reactor may be integrated with the first thermal energy transfer system 104. In one embodiment, the nuclear reactor may utilize a supercritical fluid in one or more coolant systems, which may then be coupled directly to the pyrolysis chamber 102, as shown in FIG. 1C. For example, a primary or intermediate coolant loop of the nuclear reactor may include a coolant fluid consisting of a supercritical fluid, such as supercritical CO2. The coolant loop of the nuclear reactor may be directly coupled to the pyrolysis reaction chamber 102 via the heat transfer element 103 of the first thermal energy transfer system 104 so as to intermix the supercritical fluid of the coolant loop of the nuclear reactor with the feedstock material 105 contained within the pyrolysis reaction chamber 102. In turn, upon transferring thermal energy from the nuclear reactor to the feedstock material 105, the thermal energy transfer system 104 may circulate the supercritical fluid coolant back to the nuclear reactor via return path of the heat transfer element 103. It is further contemplated herein that the first thermal energy transfer system 104 may include any number of filtration and/or separation elements in order to avoid transfer of feedstock and/or reaction products to the coolant system(s) of the nuclear reactor.

In another embodiment, as shown in FIG. 1A, the first heat transfer system 104 may include a heat exchanger 106 operably coupled to the interior of the pyrolysis reaction chamber 102. In this regard, the first heat transfer system 104 may transfer thermal energy (e.g., directly or indirectly) to the heat transfer fluid (e.g., liquid metal, liquid salt, gas, water, supercritical fluid and the like) contained within the heat transfer element 103. In turn, the heat transfer element 103 may transfer thermal energy from the heat transfer fluid to an additional working fluid contained within the pyrolysis reaction chamber 102, which may then serve to apply a pyrolysis reaction on the feedstock material 105 contained with the reaction chamber 102.

It is noted herein that the above description of the direct and indirect coupling between the one or more heat sources 108 and the feedstock 105 is not limiting and is provided merely for illustrative purposes. It is recognized herein that in a general sense the integration between the one or more heat sources (e.g., nuclear reactor) and the pyrolysis reaction chamber 104 may occur by transferring heat from a primary, intermediate, or ternary heat transfer system (e.g., coolant system) of the one or more heat sources 108 to the working fluid, such as supercritical $CO_2$, of the pyrolysis reaction chamber 102. It is further recognized herein that this integration may be carried out using any heat transfer systems or devices known in the art, such as, but not limited to, one or more heat transfer circuits, one or more heat sinks, one or more heat exchangers and the like.

In another embodiment, the pyrolysis reaction chamber 102 includes any pyrolysis reaction chamber 102 known in the art suitable for carrying out one or more pyrolysis reaction processes on the feedstock 105.

In one embodiment, the pyrolysis reaction chamber 102 includes a non-combustion or low-combustion pyrolysis chamber. For the purposes of the present disclosure a 'pyrolysis reaction' may encompass any thermochemical reaction chamber suitable for carrying out the thermochemical decomposition of organic molecules in the absence of oxygen or in a low oxygen environment.

In one embodiment, the pyrolysis reaction chamber 102 includes a fast pyrolysis chamber suitable for converting feedstock 105, such as coal or biomass, to a pyrolysis reaction product, such as tar and/or one or more non-condensable gases (NCGs). For example, the one or more NCGs outputted by the pyrolysis reaction chamber 102 may include, but are not limited to, molecular hydrogen ($H_2$), carbon monoxide (CO), carbon dioxide ($CO_2$), methane ($CH_4$), ethane ($C_2H_6$) and the like.

A fast pyrolysis reaction chamber may include any thermochemical reaction chamber capable of carrying out a thermochemical decomposition of organic molecules in the absence of oxygen (or in a reduced oxygen environment) within approximately two seconds. Fast pyrolysis is generally described by Roel J. M. Westerhof et al. in "Effect of Temperature in Fluidized Bed Fast Pyrolysis of Biomass: Oil Quality Assessment in Test Units," *Industrial & Engineering Chemistry Research*, Volume 49 Issue 3 (2010), pp. 1160-1168, which is incorporated herein by reference in the entirety. Pyrolysis and fast pyrolysis are also generally described by Ayhan Demirbas et al. in "An Overview of Biomass Pyrolysis," *Energy Sources*, Volume 24 Issue 3 (2002), pp. 471-482, which is incorporated herein by reference in the entirety.

In another embodiment, the pyrolysis reaction chamber 102 includes a supercritical pyrolysis reactor suitable for converting feedstock 105, such as biomass, to a pyrolysis reaction product, such as tar and/or one or more NCGs. For the purposes of the present disclosure, a 'supercritical pyrolysis reactor' is interpreted to encompass any reactor, reaction vessel or reaction chamber suitable for carrying out a pyrolysis reaction of feedstock material using the thermal energy supplied from a supercritical fluid. Supercritical pyrolysis methods and systems are described in U.S. patent application Ser. No. 14/209,798 to Walter et al., filed on Mar. 13, 2014, which is incorporated above in the entirety.

In another embodiment, the thermochemical reaction chamber 104 may include, but is not limited to, a fluidized bed reactor.

Combustion of feedstock may be avoided, or at least reduced, by employing an external heat source (e.g., heat source 108), such as a nuclear reactor, to supply thermal energy to drive the pyrolysis reaction (or any other thermal decomposition process) of system 100. Further, as noted previously herein, the use of a supercritical fluid, such as supercritical $CO_2$, as the working fluid in the pyrolysis reaction chamber 102 may drive pyrolysis in the feedstock material without generating excessive temperatures commonly associated with combustion-driven pyrolysis reactions.

In one embodiment, the pyrolysis reaction chamber 102 may include a pyrolysis reaction chamber (e.g., fast pyrolysis reactor or supercritical pyrolysis reactor) for thermally decomposing the feedstock 105 into one or more pyrolysis reaction products, at a temperature between approximately 350° and 600° C., using the thermal energy transferred from the volume of the heat transfer fluid contained within the heat transfer element 103. For example, the pyrolysis reaction chamber 102 may include a fast pyrolysis reactor for thermally decomposing the feedstock 105 at a temperature between approximately 350° to 600° C. using the thermal energy transferred from a nuclear reactor via the volume of heat transfer fluid, such as a supercritical fluid (e.g., supercritical $CO_2$), contained within the heat transfer element 103. By way of example, the pyrolysis reaction chamber 102 may include, but is not limited to, a supercritical pyrolysis reactor for thermally decomposing the feedstock 105 at a temperature between approximately 350° to 600° C. using the thermal energy transferred from a nuclear reactor via the volume of a supercritical fluid (e.g., supercritical $CO_2$), contained within the heat transfer element 103.

In another embodiment, the system 100 may include a char storage unit 150. In one embodiment, the char storage unit 150 is operably coupled to the output of the pyrolysis (e.g., separated output) and configured to receive char resulting from the pyrolysis reaction of the feedstock 105.

Referring again to FIG. 1A, in one embodiment, the system 100 includes a second thermal energy transfer system 118 in thermal communication with an outlet of the pyrolysis reaction chamber 102 and an internal heat source, such a water-gas-shift (WGS) reactor 120. In one embodiment, the second thermal energy transfer system 118 includes a heat transfer element 125 configured to transfer thermal energy from within the water-gas-shift reactor 120 to a heating element 122 in order to super-heat the one or more pyrolysis reaction products (e.g., tar, $H_2$, CO, $CO_2$, $CH_4$, $O_2H_6$ and the like) outputted from the pyrolysis reaction chamber 102. In one embodiment, the heat transfer element 125 may include, but is not limited to, a heat transfer loop, a heat transfer line and the like.

In one embodiment, the second heat transfer system 118 may include a first heat exchanger disposed within the WGS reactor 120 and arranged to transfer heat from the exothermic WGS reaction of the WGS reactor 120 to the heat transfer fluid of the heat transfer element 125. For example, the WGS reactor 120 may transfer thermal energy to the heat transfer fluid at a temperature in the range of approximately 600° to 700° C. In another embodiment, the heating element 122 of the second heat transfer system 118 may include a second heat exchanger disposed proximate to the output of the pyrolysis reaction chamber 102 and configured to super-heat the one or more pyrolysis reaction outputted from the pyrolysis reaction chamber 102.

The heat transfer element 125, such as a heat transfer loop, of the second thermal energy transfer system 118 may include any heat transfer fluid known in the art for transferring thermal energy from a WGS reactor to an additional sub-system. For example, the heat transfer fluid of the heat transfer element 125 of the second thermal energy transfer system 118 may include, but is not limited to, water, a pressurized gas, a liquid metal, a molten salt, a supercritical fluid and the like.

In another embodiment, system 100 includes a steam generator 124 configured to generate super-heated steam. In one embodiment, the steam generator 124 includes an outlet arranged to mix super-heated steam generated by the steam generator 124 with the super-heated pyrolysis reaction products. For example, the output of the steam generator 124 may be placed in fluidic communication with the output of the pyrolysis reaction chamber 102 via three-way valve 129, allowing for the mixing of the super-heated steam and super-heat pyrolysis reaction products.

In another embodiment, the steam generator 124 is arranged to receive a volume of saturated steam via the combination of thermal energy from one or more downstream internal heat sources (e.g., WGS 120 and methanol reactor 138) and water from an external water source 140. For example, an inlet of the steam generator 124 may be placed in fluidic communication with the external water source and is arranged to receive a volume of saturated steam (e.g., T=100° C.) following conversion of water from the external water source 140 to saturated steam via heat supplied from the one or more downstream internal heat sources.

In another embodiment, the heat transfer element 125 of the second thermal energy transfer system 118 is further configured to transfer thermal energy from within the water-gas-shift reactor 120 to an additional heating element 123 in order to transfer thermal energy to the water from the cold water source 140 so to produce saturated steam, which is then transferred to steam generator 124, discussed in further detail further herein.

In another embodiment, the steam generator 124 is configured to supply thermal energy to the saturated steam in order form super-heated steam for mixing with the super-heated pyrolysis product. For example, the steam generator 124 may generate super-heated steam at a temperature between 650° and 750° C. In another embodiment, the steam generator 124 may receive thermal energy from a downstream internal heat source (e.g., steam reformer supplying). For example, the steam generator 124 may receive thermal energy at a temperature between 650° and 750° C. from an internal downstream heat source, such as a steam reformer 126, as discussed in greater detail further herein.

In another embodiment, the steam reformer 126 is placed in fluidic communication with the outlet of the pyrolysis reaction chamber and the steam generator (e.g., via three-way valve 129). In another embodiment, following mixing of the super-heated pyrolysis reaction products and the super-heated steam, a mixed output 119 may be supplied to the steam reformer 126. In one embodiment, the mixed output 119 may include, but is not limited to, steam, tar and one or more NCGs. In another embodiment, the mixed output 119 may include, but is not limited to, steam, tar and one or more NCGs having a temperature between approximately 650° and 750° C.

In another embodiment, the steam reformer 126 is configured to convert the mixed product 119, consisting of the super-heated pyrolysis reaction product and the super-heated steam, to one or more reformed products. In one embodiment, the one or more reformed products 127 outputted from the steam reformer may include, but are not limited to, $H_2$ and CO. It is noted herein that steam reforming may serve to react steam at high temperature with one or more initial hydrocarbon products to generate hydrogen. For example, in the case of methane ($CH_4$), the steam reformer may react steam water with methane to form an output of carbon monoxide and molecular hydrogen ($H_2$) as shown below:

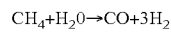

$$CH_4 + H_2O \rightarrow CO + 3H_2$$

In one embodiment, it is further noted that, in addition to CO and $H_2$, additional compounds may be present in the product stream following the reformer due to unreacted compounds, such as NCGs, leaving the reformer. For example, the output of the steam reformer 126 may include NCGs, such as $CO_2$, in addition to CO and $H_2$. It is further noted herein that reaction described above is not limiting. Rather, the above description is provided merely for illustrative purposes and it is contemplated herein that any steam reforming process known in the art may be applied to the mixed product 119 to generate one or more reformed products.

In another embodiment, the steam reformer 126 is configured to transfer thermal energy to the steam generator 124, as previously described. In one embodiment, the system 100 includes a third thermal energy transfer system 160 in thermal communication with the steam reformer 126 and the steam generator 124. In one embodiment, the third thermal energy transfer system 160 includes a heat transfer element 128. In one embodiment, the heat transfer element 128 may include, but is not limited to, a heat transfer loop, a heat transfer line and the like. For example, the heat transfer element 128 may include, but is not limited to, a heat transfer loop filled with a heat transfer fluid (e.g., pressurized heat transfer fluid) and placed in thermal communication (e.g., directly or indirectly) with one or more portions of the steam reformer 126 and the steam generator 124. For instance, the heat transfer fluid may include, but is not limited to, a liquid (e.g., liquid metal or molten salt), a gas (e.g., pressurized gas), water or supercritical fluid (e.g., super critical carbon dioxide). In another embodiment, the third thermal energy transfer system 160 includes one or more heat exchangers. For example, the third energy transfer system 160 may include a first heat exchanger for transferring thermal energy (e.g., thermal energy at a temperature in the range of 650° to 750° C.) from the steam reformer 126 to the heat transfer fluid of the heat transfer element 128. Further, the third heat transfer system 160 may include a second heat exchanger for transferring thermal energy from the heat transfer fluid of the heat transfer element 128 to the working fluid of steam generator 124, which is then used to generate super-heated steam, as described previously herein.

In another embodiment, the steam reformer 126 is configured to receive thermal energy from a downstream internal heat source (e.g., compression system 131), as discussed in greater detail further herein. It is noted herein that the steam reformer 126 may receive thermal energy at a high temperature, such as a temperature between 800° and 950° C., via a heat transfer fluid coupled to a downstream internal heat source. In another embodiment, the thermal energy contained in the heat transfer fluid is partially transferred to the mixed product 119 during the steam reforming process. As a result, the heat transfer fluid outputted from the steam reformer and transferred to the steam generator has reduced thermal energy and, therefore, lower temperature, relative to the input fluid. For example, as discussed above, the steam reformer 126 may transfer thermal energy to the steam generator 124 at a temperature in the range of 650° to 750° C.

In another embodiment, water-gas-shift reactor 120 is placed in fluidic communication with an outlet of the steam reformer 126 and is configured to receive an output 127 of the steam reformer 126. In another embodiment, the water-gas-shift reactor 120 is suitable for converting at least a portion of the one or more reformed products 127 from the steam reformer 126 to one or more synthesis gas products via a water-gas-shift reaction. It is noted herein that a water-gas-shift reaction includes the reaction of carbon monoxide with water vapor. For example, a water-gas-shift reaction of carbon may take the form:

$$CO + H_2O \rightarrow CO_2 + H_2$$

In one embodiment, the reaction products of water-gas-shift reactor 120 serve to form the components of synthesis gas. In one embodiment, synthesis gas includes, but is not limited to, CO and $H_2$. In another embodiment, synthesis gas includes, but is not limited to, CO, $H_2$ and $CO_2$. It is noted herein that any water-gas-shift reaction process suitable for producing synthesis gas may be implemented by system 100.

In another embodiment, as noted previously herein, thermal energy from the water-gas-shift reaction of the water-gas-shift reactor 120 may be transferred to the heating element 122 (used to super-heat the one or more pyrolysis reaction products) and heating element 123 (used to form saturated steam prior for use by the steam generator 124).

In another embodiment, the compression system 131 is placed in fluidic communication with an outlet of the water-gas-shift reactor 120. In one embodiment, the compression system 131 is configured to compress the synthesis gas product 121 outputted from the water-gas-shift reactor 120 in at least one compression phase. In one embodiment, the compression system 131 includes a first compressor 134 in fluidic communication with an outlet of the water-gas-shift reactor 120 and configured to compress the synthesis gas product 121 in a first compression phase. For example, the first compression phase may include compressing the synthesis gas product from an input pressure in the range of 20-100 atm to an output pressure in the range of 2500-4500 atm. Further, the large increase in pressure leads to a large temperature increase, whereby the temperature may increase from an input temperature of approximately 400°-600° C. to an output temperature of 800°-1000° C.

In another embodiment, following the first compression phase, the system 100 may extract thermal energy. In one embodiment, the third thermal energy transfer system 160 includes a first heat exchanger 130 configured to extract thermal energy from the synthesis gas product during the first compression phase. In another embodiment, the third thermal energy transfer system 160 is configured to transfer the extracted thermal energy to the steam reformer 126 via the heat transfer fluid contained in the heat transfer element 128.

In another embodiment, the compression system 131 includes a second compressor 136 in fluidic communication with an outlet of the first compressor 134 and configured to compress the synthesis gas product 121 in a second compression phase. For example, the second compression phase may include compressing the synthesis gas product from an input pressure in the range of 2.0 to 10.0 atm to an output pressure in the range of 25.0 to 45.0 atm. Again, the large increase in pressure during the second compression phase leads to a large temperature increase, whereby the temperature may increase from an input temperature of approximately 200°-500° C. to an output temperature of 800°-1000° C. It is noted herein that the values provided above for temperature and pressure ranges during the first and second compression phases are not limiting and should be interpreted merely as illustrative.

In another embodiment, following the second compression phase, the system 100 may again extract thermal energy. In one embodiment, the third thermal energy transfer system 160 includes a second heat exchanger 132 configured to extract thermal energy from the synthesis gas product during the second compression phase. In another embodiment, the third thermal energy transfer system 160 is configured to transfer the extracted thermal energy to the steam reformer 126 via the heat transfer fluid contained in the heat transfer element 128.

In another embodiment, the system 100 includes a methanol reactor 138 placed in fluidic communication with an outlet of the compression system and configured to convert the compressed at least one synthesis gas product to a volume of methanol. It is noted herein that any syngas-to-methanol conversion process known in the art may be utilized by methanol reactor 138. It is further noted herein that syngas-to-methanol conversion is generally dictated by the following reactions:

$$CO_2 + 3H_2 \rightarrow CH_3OH + H_2O$$

$$CO + 2H_2 \rightarrow CH_3OH$$

$$CO_2 \rightarrow CO + H_2O$$

In one embodiment, the system 100 includes a fourth thermal energy transfer system 142 in thermal communication with the methanol reactor 138 and a volume of water from the external water source 140. In another embodiment, the fourth energy transfer system 142 is arranged to transfer thermal energy from the exothermic syngas-to-methanol reaction carried out in the methanol reactor 138 to the water from the external water source 140 to form saturated steam for use by the steam generator 124 in forming super-heated steam. For example, the fourth thermal energy transfer system 142 may include a heat transfer element 145 (e.g., heat transfer loop) containing a heat transfer fluid (similar to the various heat transfer elements described previously herein) suitable for transfer thermal energy from the methanol reactor 138 (e.g., via heat exchanger 138) to the heating exchanger 144 configured to heat the water from the external water source 140, as described previously herein.

In another embodiment, the system 100 includes a methanol-to-gasoline (MTG) reactor 146 in fluidic communication with an outlet of the methanol reactor 138 and configured to convert at least a portion of the volume of methanol to a volume of gasoline. It is noted herein that the MTG reactor 146 may include any methanol-to-gasoline reactor known in the art. In another embodiment, the gasoline product generated by the MTG reactor 146 may be stored in the storage unit 148.

FIG. 1D illustrates system 100 equipped with a char burner 154. In one embodiment, the char burner 154 is operably coupled to an output of the pyrolysis chamber 102. In another embodiment, the char burner 154 is configured to receive a volume of char from the pyrolysis chamber 102. In another embodiment, the char burner 154 is suitable for burning the received volume of char. In another embodiment, the char burner 154 is in thermal communication with the steam reformer 126 and configured to supply thermal energy to the steam reformer 126.

In another embodiment, system 100 includes an additional steam generator 152. In one embodiment, the additional steam generator 152 is in thermal communication with a portion of the one or more heat sources 108 and is configured to convert a supply of water to steam using thermal energy supplied from the one or more heat sources 108. In another embodiment, the steam output 156 of the steam generator may be supplied to one or more sub-systems (e.g., steam reformer) of system 100.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Figure 2:
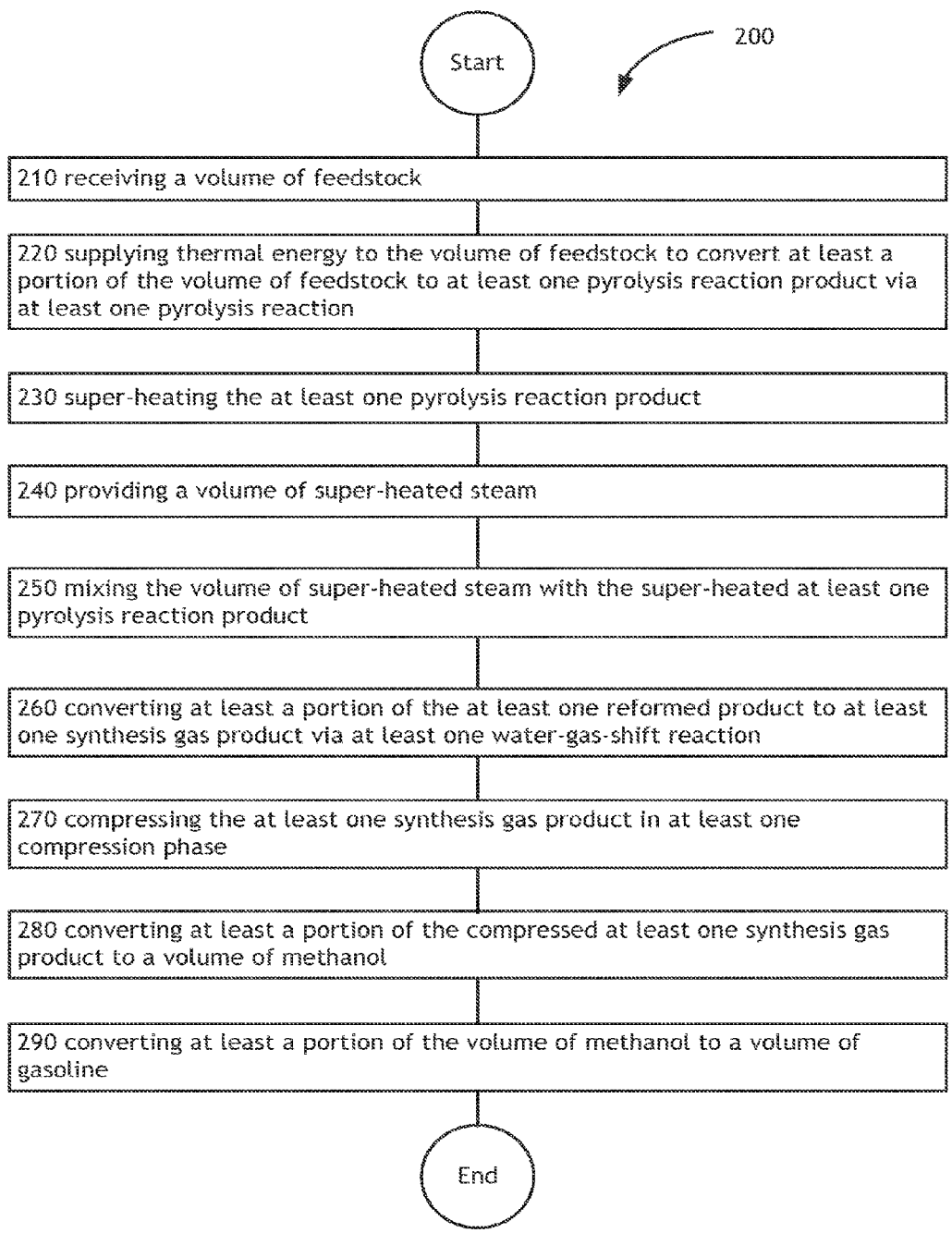
FIG. 2 is a high-level flowchart of a method for performing gasification of a carbonaceous feedstock material.

FIG. 2 illustrates an operational flow 200 representing example operations related gasification of carbonaceous feedstock. In FIG. 2 and in following figures that include various examples of operational flows, discussion and explanation may be provided with respect to the above-described examples of FIGS. 1A through 1D, and/or with respect to other examples and contexts. However, it should be understood that the operational flows may be executed in a number of other environments and contexts, and/or in modified versions of FIGS. 1A through 1D. Also, although the various operational flows are presented in the sequence(s) illustrated, it should be understood that the various operations may be performed in other orders than those which are illustrated, or may be performed concurrently.

After a start operation, the operational flow 200 moves to feedstock receiving operation 210. The feedstock receiving operation 210 depicts receiving a volume of feedstock. For example, as shown in FIGS. 1A through 1D, the pyrolysis reaction chamber may receive one or more feedstock materials 105 from a feedstock supply 110 via a feedstock supply system 111. By way of another example, feedstock from the feedstock supply 110 may be processed via grinder 112 prior to pre-heating by pre-heater 116 and entry into the pyrolysis reaction chamber 102. Further, the one or more feedstock materials may include, but are not limited to, a carbonaceous material, such as, but not limited to, coal, biomass, mixed-source biomaterial, plastic, refuse and landfill waste.

Then, energy supplying operation 220 depicts supplying thermal energy to the volume of feedstock to convert at least a portion of the volume of feedstock to at least one pyrolysis reaction product via at least one pyrolysis reaction. For example, as shown in FIGS. 1A through 1D, thermal energy generated by one or more heat sources 108 may be transferred to the volume of feedstock 105 contained within the pyrolysis reaction chamber 102 to convert a portion of the volume of feedstock 105 to one or more pyrolysis reaction products via at least one pyrolysis reaction. For instance, thermal energy may be transferred from one or more heat sources 108 in thermal communication with the pyrolysis reaction chamber 102 via a heat transfer element 103 of a first thermal energy transfer system 104 containing a supercritical fluid working fluid. Further, the one or more heat sources 108 may include, but are not limited to, one or more nuclear reactors, such as, but not limited to, a molten salt cooled nuclear reactor, a liquid metal cooled reactor, a gas cooled reactor or a supercritical fluid cooled reactor.

Then, super-heating operation 230 depicts super-heating the at least one pyrolysis reaction product. For example, as shown in FIGS. 1A through 1D, the second thermal energy system 118 may transfer thermal energy from the water-gas-shift reaction of the water-gas-shift reactor 120 to a heating element 122 (e.g., heat exchanger) in order to super-heat the pyrolysis reaction product(s) outputted from the pyrolysis reaction chamber 102.

Then, the steam providing operation 240 depicts providing a volume of super-heated steam. For example, as shown in FIGS. 1A through 1D, steam generator 124 may provide super-heated steam. For instance, the steam generator 124 may receive a volume of saturated steam and convert at least a portion of saturated steam to super-heated steam.

Then, the mixing operation 250 depicts mixing the volume of super-heated steam with the super-heated at least one pyrolysis reaction product. For example, as shown in FIGS. 1A through 1D, three-way valve 129 may mix, or combine, a volume of the super-heated steam from the steam generator 124 and a volume of the super-heated pyrolysis reaction product.

Then, converting operation 260 depicts converting at least a portion of the at least one reformed product to at least one synthesis gas product via at least one water-gas-shift reaction. For example, as shown in FIGS. 1A through 1D, a water-gas-shift reactor 120 may convert one or more reformed products received from the steam reformer 126 to one or more synthesis gas products 121 via a water-gas-shift reaction.

Then, compressing operation 270 depicts compressing the at least one synthesis gas product in at least one compression phase. For example, as shown in FIGS. 1A through 1D, a compression system 131 may compress the synthesis gas product received from the water-gas-shift reactor 120.

Then, syngas-to-methanol converting operation 280 depicts converting at least a portion of the compressed at least one synthesis gas product to a volume of methanol. For example, as shown in FIGS. 1A through 1D, a methanol reactor 138 may convert the synthesis gas received from compression system 131 to methanol.

Then, methanol-to-MTG converting operation 290 depicts converting at least a portion of the volume of methanol to a volume of gasoline. For example, as shown in FIGS. 1A through 1D, a MTG reactor 146 may convert the methanol received from the methanol reactor 138 to gasoline 148.

Figure 3:
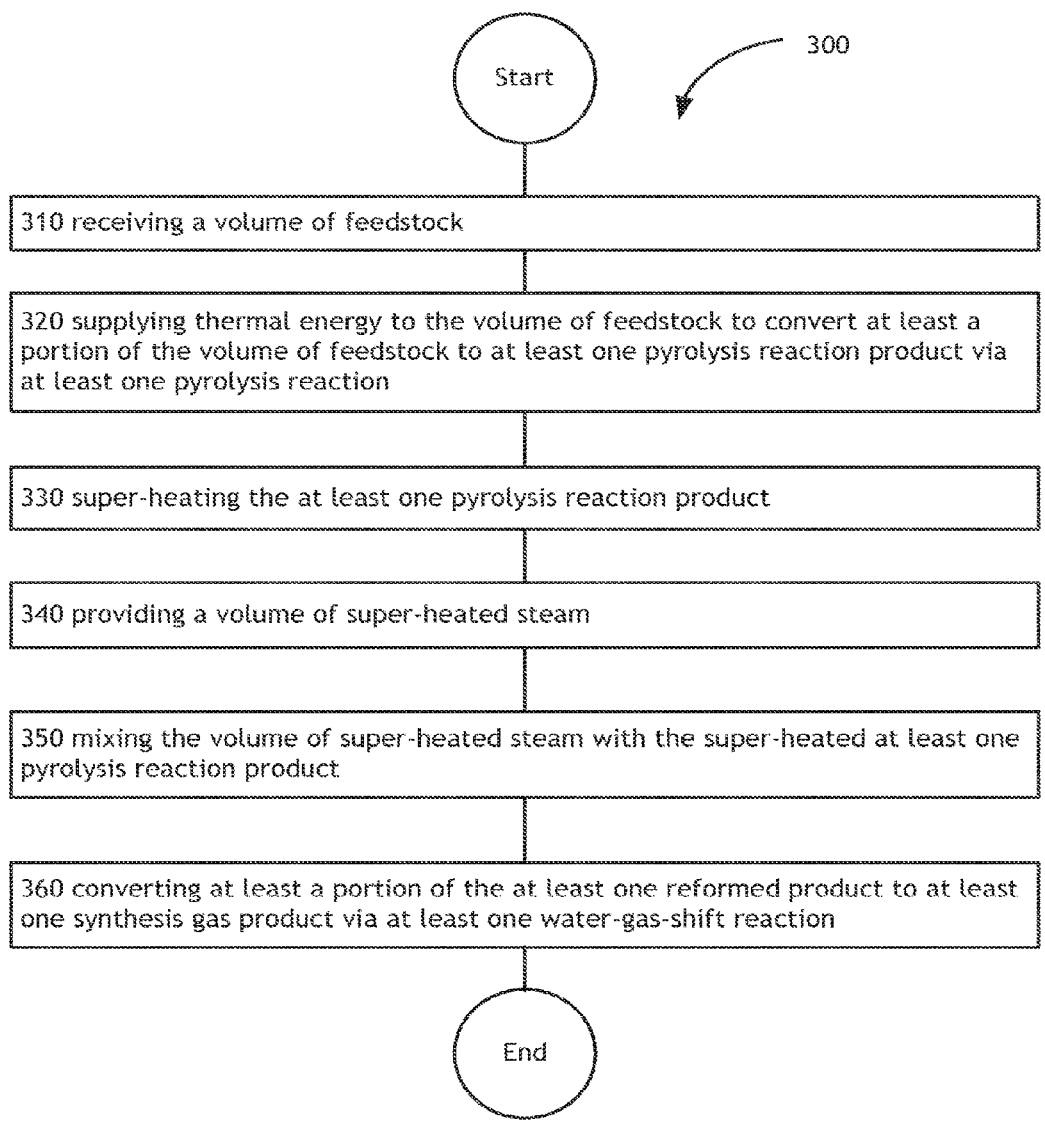
FIGS. 3 through 9 are high-level flowcharts depicting alternate implementations of FIG. 2.
Figure 4:
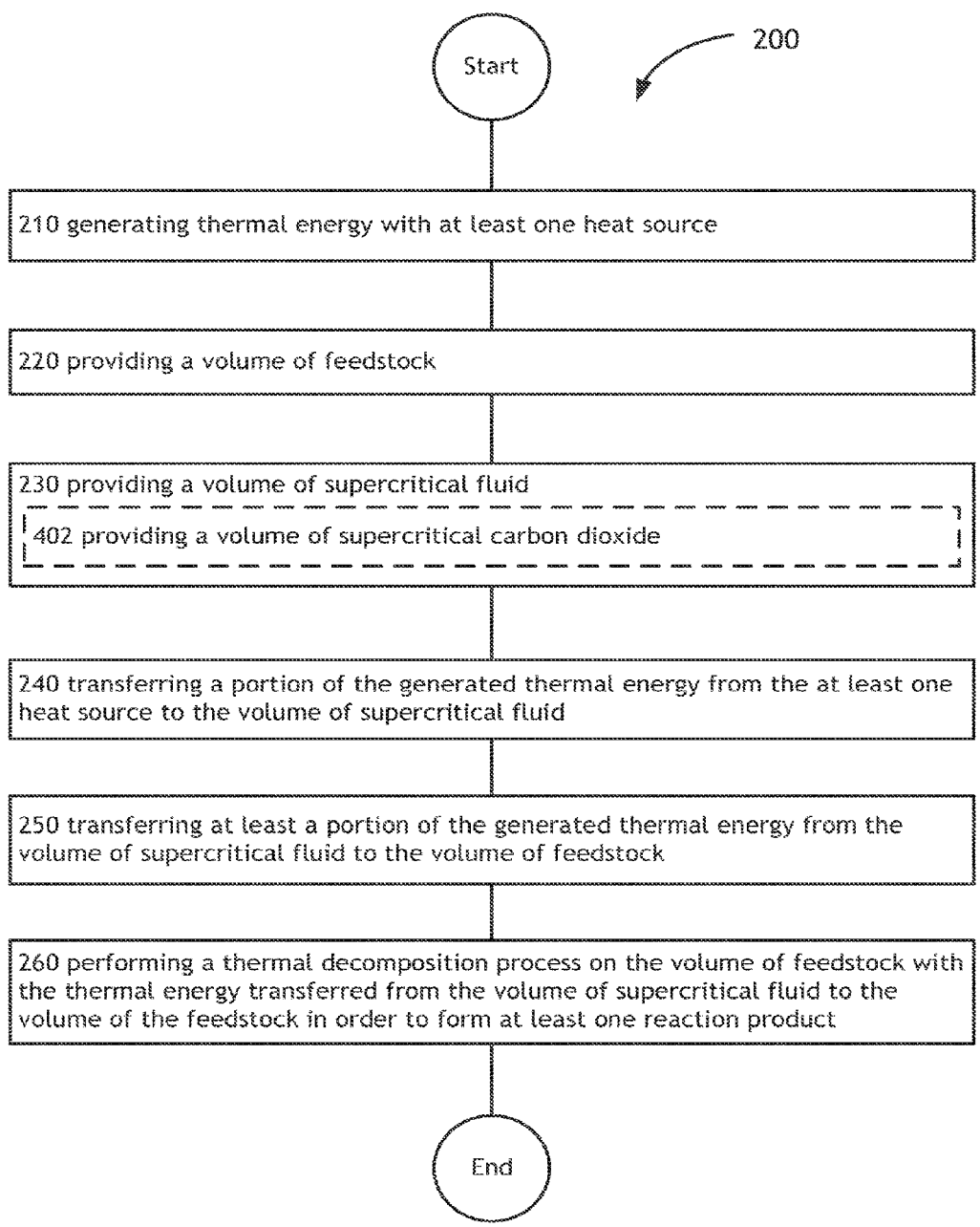
Figure 5:
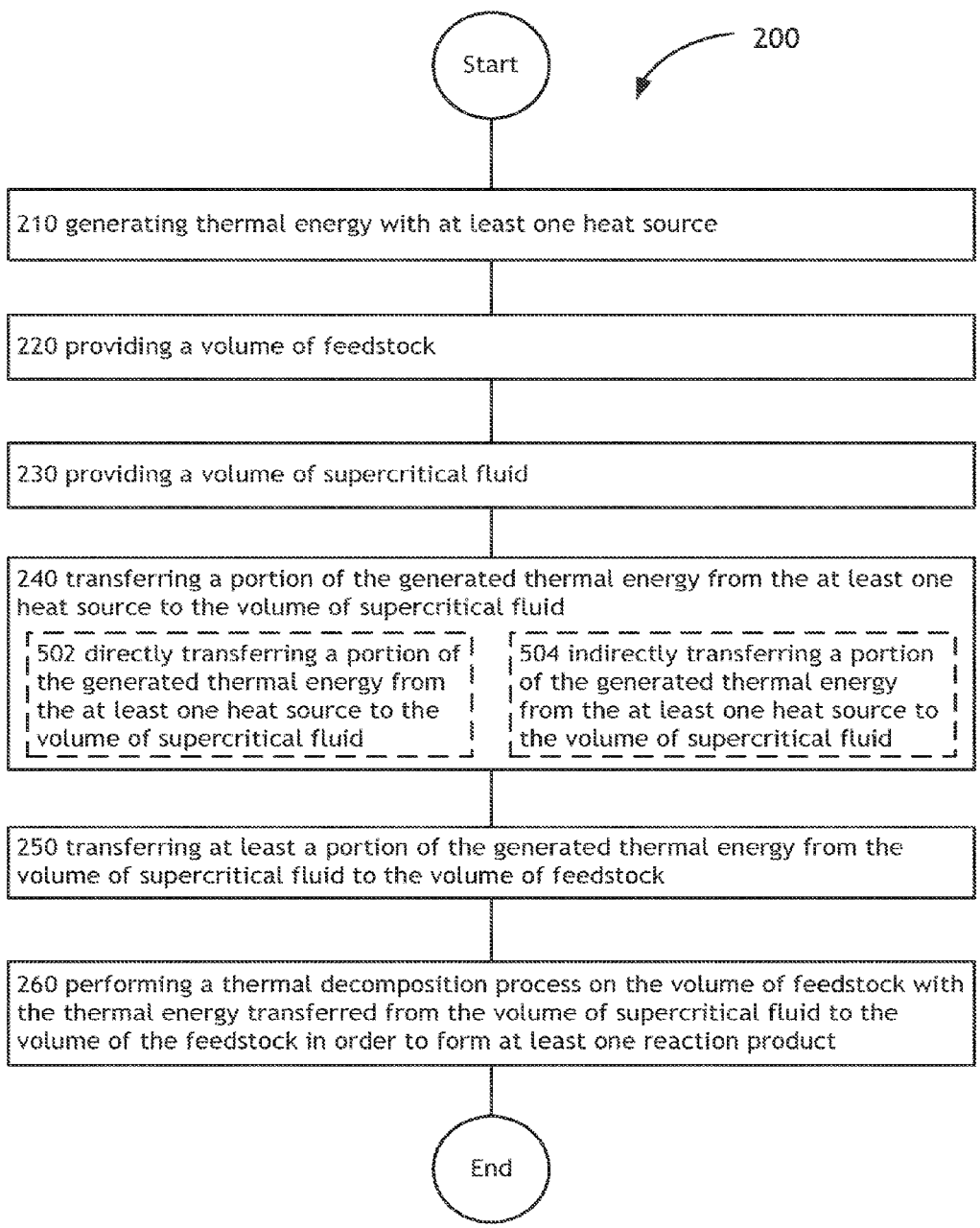
Figure 6:
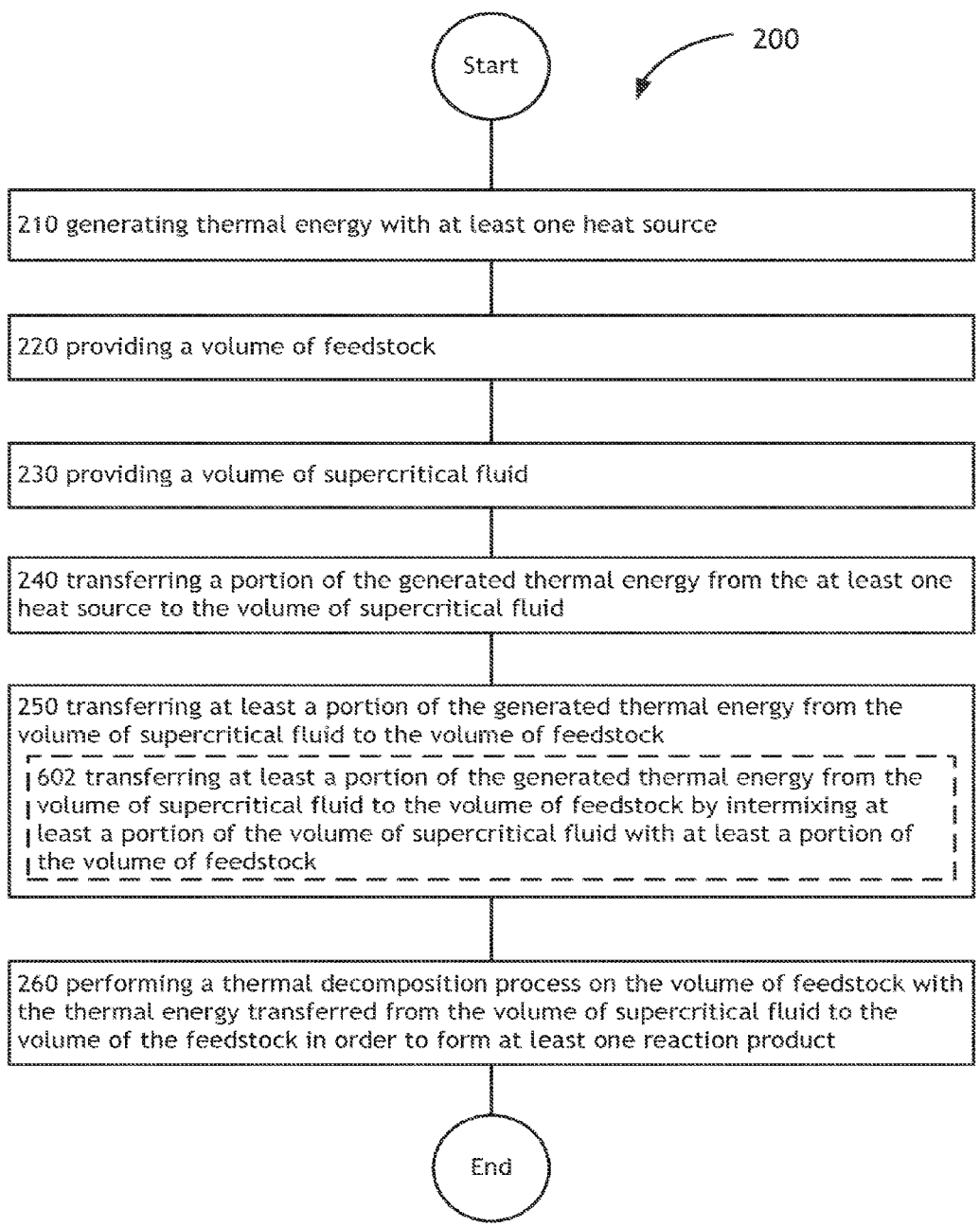
Figure 7:
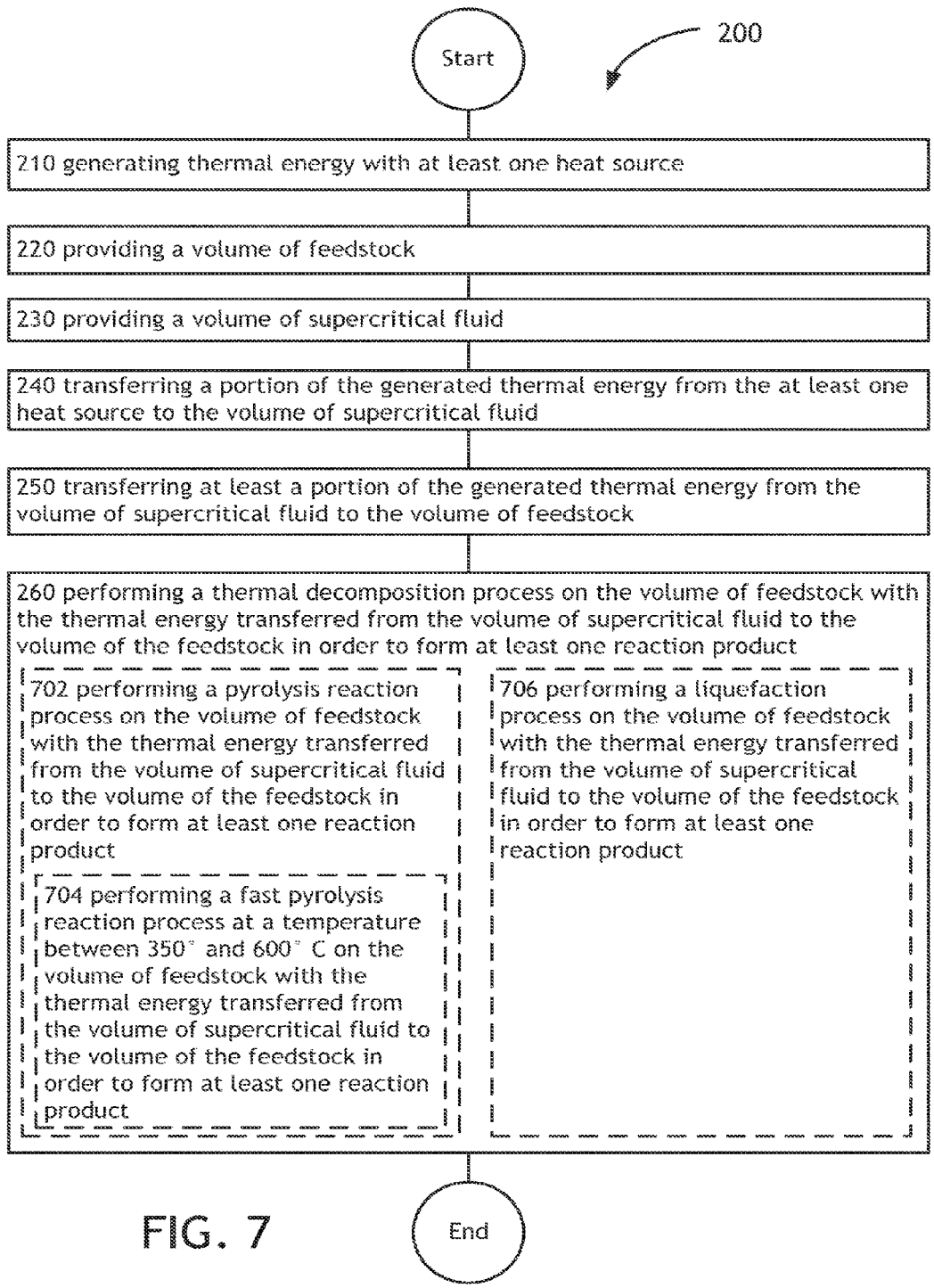
Figure 8:
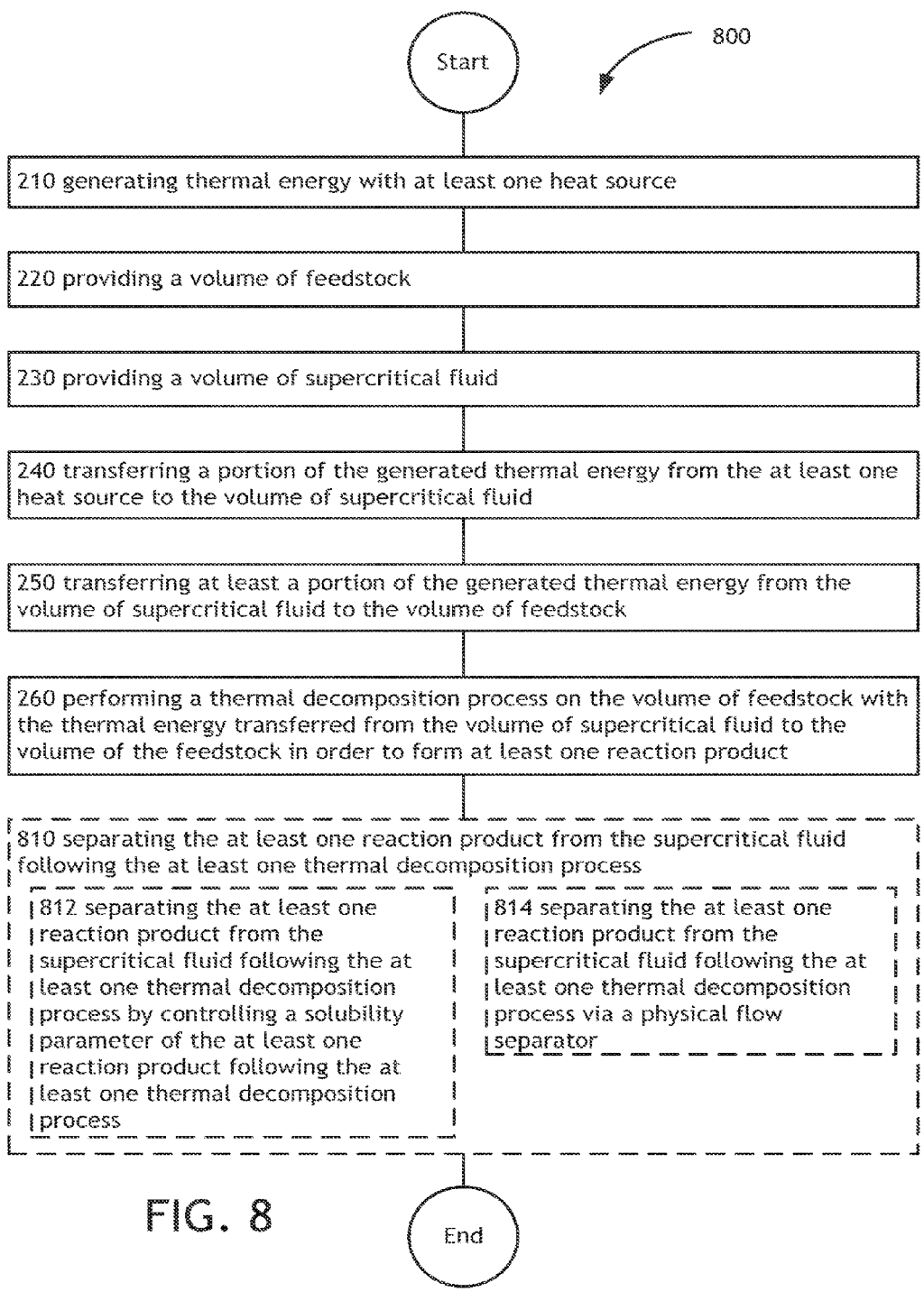
Figure 9:
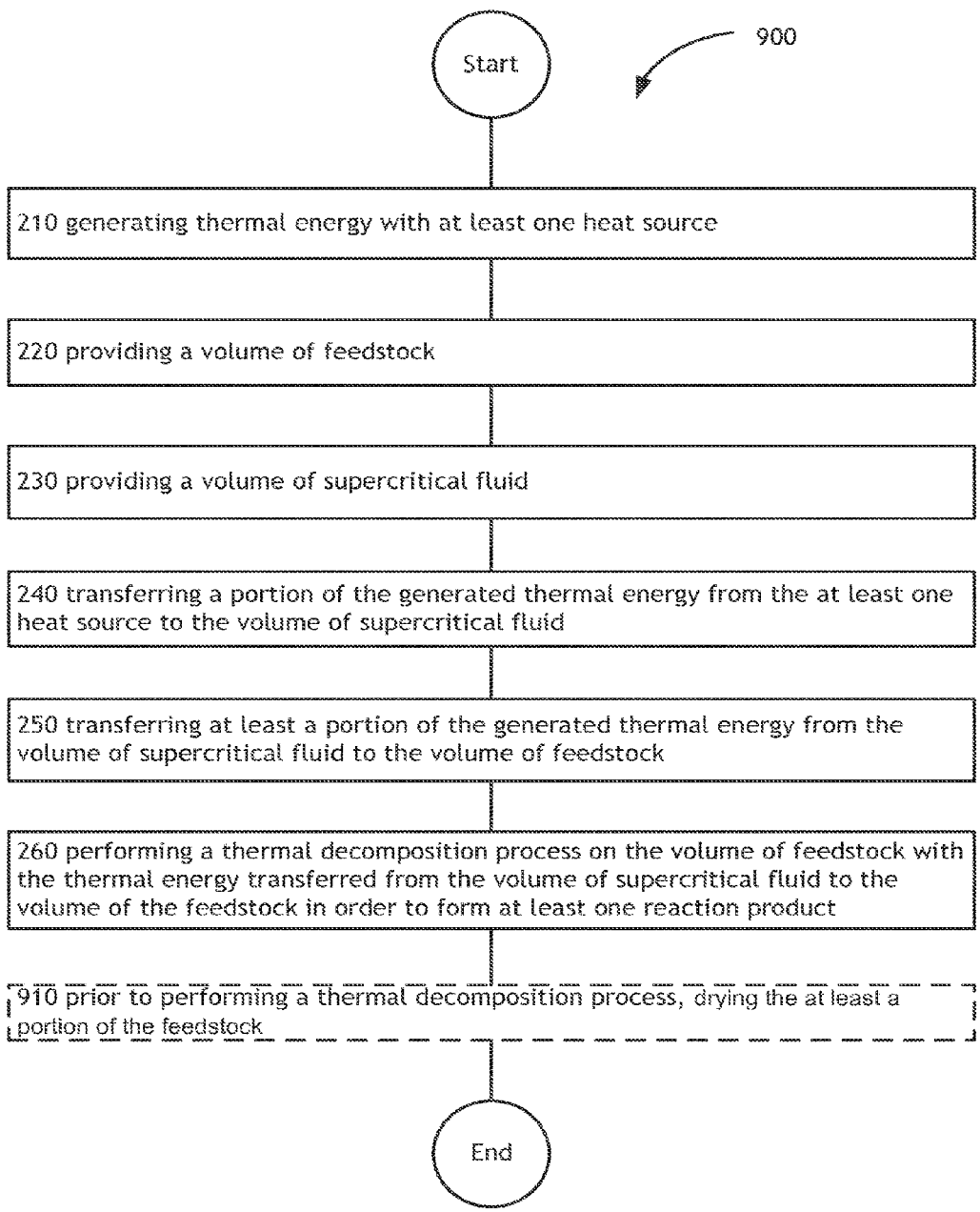

FIG. 3 illustrates an operational flow 300 representing example operations related to generating a nuclear reactor core loading distribution. After a start operation, the operational flow 300 moves to feedstock receiving operation 310. The feedstock receiving operation 310 depicts receiving a volume of feedstock. For example, as shown in FIGS. 1A through 1D, the pyrolysis reaction chamber may receive one or more feedstock materials 105 from a feedstock supply 110 via a feedstock supply system 111. By way of another example, feedstock from the feedstock supply 110 may be process via grinder 112 prior to pre-heating by pre-heater 116 and entry into the pyrolysis reaction chamber 102. Further, the one or more feedstock materials may include, but are not limited to, a carbonaceous material, such as, but not limited to, coal, biomass, mixed-source biomaterial, plastic, refuse and landfill waste.

Then, energy supplying operation 320 depicts supplying thermal energy to the volume of feedstock to convert at least a portion of the volume of feedstock to at least one pyrolysis reaction product via at least one pyrolysis reaction. For example, as shown in FIGS. 1A through 1D, thermal energy generated by one or more heat sources 108 may be transferred to the volume of feedstock 105 contained within the pyrolysis reaction chamber 102 to convert a portion of the volume of feedstock to one or more pyrolysis reaction products via at least one pyrolysis reaction. For instance, thermal energy may be transferred from one or more heat sources 108 in thermal communication with the pyrolysis reaction chamber 102 via a heat transfer element 103 of a first thermal energy transfer system 104 containing a supercritical fluid working fluid. Further, the one or more heat sources 108 may include, but are not limited to, one or more nuclear reactors, such as, but not limited to, a molten salt cooled nuclear reactor, a liquid metal cooled reactor, a gas cooled reactor or a supercritical fluid cooled reactor.

Then, super-heating operation 330 depicts super-heating the at least one pyrolysis reaction product. For example, as shown in FIGS. 1A through 1D, the second thermal energy system 118 may transfer thermal energy from the water-gas-shift reaction of the water-gas-shift reactor 120 to a heating element 122 (e.g., heat exchanger) in order to super-heat the pyrolysis reaction product(s) outputted from the pyrolysis reaction chamber 102.

Then, the steam providing operation 340 depicts providing a volume of super-heated steam. For example, as shown in FIGS. 1A through 1D, steam generator 124 may provide super-heated steam. For instance, the steam generator 124 may receive a volume of saturated steam and convert at least a portion of saturated steam to super-heated steam.

Then, the mixing operation 350 depicts mixing the volume of super-heated steam with the super-heated at least one pyrolysis reaction product. For example, as shown in FIGS. 1A through 1D, three-way valve 129 may mix, or combine, a volume of the super-heated steam from the steam generator 124 and a volume of the super-heated pyrolysis reaction product.

Then, converting operation 360 depicts converting at least a portion of the at least one reformed product to at least one synthesis gas product via at least one water-gas-shift reaction. For example, as shown in FIGS. 1A through 1D, a water-gas-shift reactor 120 may convert one or more reformed products received from the steam reformer 126 to one or more synthesis gas products 121 via a water-gas-shift reaction.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit device-detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled//implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although a user is shown/described herein as a single illustrated figure, those skilled in the art will appreciate that the user may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

The invention claimed is:

1. An apparatus comprising:
   a pyrolysis reaction chamber for containing a volume of feedstock;
   a first thermal energy transfer system in thermal communication with the pyrolysis reaction chamber and at least one heat source for converting at least a portion of the volume of feedstock to at least one pyrolysis reaction product;
   a second thermal energy transfer system in thermal communication with an outlet of the pyrolysis reaction chamber and an internal heat source for super-heating the at least one pyrolysis reaction product;
   a steam generator including an outlet arranged to mix super-heated steam with the super-heated at least one pyrolysis reaction product;
   a steam reformer in fluidic communication with the outlet of the pyrolysis reaction chamber and the steam generator, the steam reformer configured to convert the super-heated at least one pyrolysis reaction product and the super-heated steam to at least one reformed product;
   a water-gas-shift reactor in fluidic communication with an outlet of the steam reformer and configured to convert at least a portion of the at least one reformed product to at least one synthesis gas product via at least one water-gas-shift reaction;
   a compression system in fluidic communication with an outlet of the water-gas-shift reactor and configured to compress the at least one synthesis gas product in at least one compression phase;
   a methanol reactor in fluidic communication with an outlet of the compression system and configured to convert at least a portion of the compressed at least one synthesis gas product to a volume of methanol; and
   a methanol-to-gasoline reactor in fluidic communication with an outlet of the methanol reactor and configured to convert at least a portion of the volume of methanol to a volume of gasoline.

2. The apparatus of claim 1, wherein the feedstock includes:
   a carbonaceous material.

3. The apparatus of claim 2, wherein the feedstock includes:
   at least one of coal, biomass, mixed-source biomaterial, plastic, refuse, and landfill waste.

4. The apparatus of claim 1, wherein the at least one heat source includes:
   at least one nuclear reactor.

5. The apparatus of claim 4, wherein the at least one nuclear reactor includes:
   at least one of a molten salt cooled nuclear reactor system, a liquid metal cooled reactor system, a gas cooled reactor system and a supercritical fluid cooled reactor system.

6. The apparatus of claim 1, wherein the first thermal energy transfer system includes:
   a direct heat exchange system.

7. The apparatus of claim 1, wherein the first thermal energy transfer system includes:
   an indirect heat exchange system.

8. The apparatus of claim 1, wherein the first thermal energy transfer system includes:
   a heat transfer element containing a working fluid of the at least one heat source.

9. The apparatus of claim 8, wherein the working fluid includes:
   a supercritical fluid.

10. The apparatus of claim 1, wherein the internal heat source is the water-gas-shift reactor.

11. The apparatus of claim 1, wherein the at least one pyrolysis reaction product includes:
    at least one of tar and a non-condensable gas.

12. The apparatus of claim 11, wherein the non-condensable gas includes:
    at least one of molecular hydrogen, carbon monoxide, carbon dioxide, methane and ethane.

13. The apparatus of claim 1, wherein the compression system in fluidic communication with an outlet of the water-gas-shift reactor and configured to compress the at least one synthesis gas product in at least one compression phase includes:
    a first compressor in fluidic communication with an outlet of the water-gas-shift reactor and configured to compress the at least one synthesis gas product in a first compression phase; and
    a second compressor in fluidic communication with an outlet of the first compressor and configured to compress the at least one synthesis gas product in a second compression phase.

14. The apparatus of claim 13, further comprising:
    a third thermal energy transfer system in thermal communication with the compression system and the steam reformer, the third thermal energy transfer system including a first heat exchanger configured to extract thermal energy from the at least one synthesis gas product during the first compression phase and at least a second heat exchanger configured to extract thermal energy from the at least one synthesis gas product during the second compression phase, wherein the third thermal energy transfer system is configured to supply the thermal energy extracted with the first heat exchanger and the thermal energy extracted with the second heat exchanger to the steam reformer.

15. The apparatus of claim 14, wherein the third thermal energy transfer system is in thermal communication with the steam generator and the steam reformer and configured to transfer thermal energy from the steam reformer to the steam generator.

16. The apparatus of claim 1, further comprising:
    an external water source; and
    a fourth thermal energy transfer system in thermal communication with the methanol reactor and a volume of water from the external water source and arranged to supply thermal energy from the methanol reactor to the volume of water from the external water source to form saturated steam.

17. The apparatus of claim 16, wherein the second thermal energy transfer system is further configured to transfer thermal energy from the internal heat source to the volume of water to form saturated steam.

18. The apparatus of claim 17, wherein an inlet of the steam generator is in fluidic communication with the external water source and is arranged to receive saturated steam, wherein the steam generator is configured to supply thermal energy to the saturated steam to form super-heated steam.

19. The apparatus of claim 1, wherein the at least one reformed product from the steam reformer includes:
   at least one of molecular hydrogen and carbon monoxide.

20. The apparatus of claim 1, wherein the at least one synthesis gas product from the water-gas-shift reactor includes:
   at least one of molecular hydrogen, carbon monoxide and carbon dioxide.

21. The apparatus of claim 1, further comprising:
   a char burner operably coupled to an output of the pyrolysis chamber and configured to burn a volume of char received from the pyrolysis chamber, wherein the char burner is in thermal communication with the steam reformer and configured to supply thermal energy to the steam reformer.

22. The apparatus of claim 1, further comprising:
   an additional steam generator in thermal communication with a portion of the at least one heat source and configured to convert a supply of water to steam.

23. The apparatus of claim 1, further comprising:
   a feedstock pre-heater.

24. An apparatus comprising:
   a pyrolysis reaction chamber for containing a volume of feedstock;
   a first thermal energy transfer system in thermal communication with the pyrolysis reaction chamber and at least one heat source for converting at least a portion of the volume of feedstock to at least one pyrolysis reaction product;
   a second thermal energy transfer system in thermal communication with an outlet of the pyrolysis reaction chamber and an internal heat source for super-heating the at least one pyrolysis reaction product, wherein the second thermal energy transfer system is located downstream from the outlet of the pyrolysis reaction chamber;
   a steam generator including an outlet arranged to mix the super-heated steam with super-heated at least one pyrolysis reaction product;
   a steam reformer in fluidic communication with the outlet of the pyrolysis reaction chamber and the steam generator, the steam reformer configured to convert the super-heated at least one pyrolysis reaction product and the super-heated steam to at least one reformed product; and
   a water-gas-shift reactor in fluidic communication with an outlet of the steam reformer and configured to convert at least a portion of the at least one reformed product to at least one synthesis gas product via at least one water-gas-shift reaction.

25. An apparatus comprising:
   a pyrolysis reaction chamber for containing a volume of feedstock;
   a first thermal energy transfer system in thermal communication with the pyrolysis reaction chamber and at least one heat source for converting at least a portion of the volume of feedstock to at least one pyrolysis reaction product;
   a second thermal energy transfer system in thermal communication with the pyrolysis reaction chamber and an internal heat source for providing thermal energy to the at least one pyrolysis reaction product, wherein the second thermal energy transfer system is located downstream from the outlet of the pyrolysis reaction chamber;
   a steam generator including an outlet arranged to mix steam with the at least one pyrolysis reaction product; and
   a steam reformer in fluidic communication with the pyrolysis reaction chamber and the steam generator, the steam reformer configured to convert the at least one pyrolysis reaction product and the steam to at least one reformed product.

26. The apparatus of claim 25, further comprising:
   a water-gas-shift reactor in fluidic communication with the steam reformer and configured to convert at least a portion of the at least one reformed product to at least one synthesis gas product via at least one water-gas-shift-reaction.

* * * * *